US00PP10935P

United States Patent [19]

Kumar et al.

[11] Patent Number: Plant 10,935

[45] Date of Patent: Jun. 1, 1999

[54] **MINI PLANT *MENTHA ARVENSIS* 'HIMALAYA'**

[75] Inventors: Sushil Kumar, Vikas Nagar; Bali Ram Tyagi, Indira Nagar; Janak Raj Bahl, Vikas Nagar; Hari Singh; Vikram Singh, both of Indira Nagar; Ram Ujagir, Kalyanpur; Suman Preet Singh Khanuja; Ajit Kumar Shasany, both of Aliganj; Ram Sajivan Shukla, Indira Nagar; Abdul Sattar, Khurram Nagar; Dwijendra Singh, Indira Nagar; Akhtar Haseeb, Vikas Nagar; Vijay Pal Singh, Gomti Nagar; Paltoo Ram, Kalyanpur; Kambod Singh, Indira Nagar; Saudan Singh, Aliganj; Surendra Pratap Singh, Vikas Nagar; Nirmal Kumar Patra, Pantnagar; Mansoor Alam, Vikas Nagar; Arif Ali Naqvi, Indira Nagar; Muni Ram, CIMAP; Krishan Kumar Agarwal, Opp. Kalyanpur; Kailash Singh, Kalyanpur, all of India

[73] Assignee: Council of Scientific & Industrial Research, New Delhi, India

[21] Appl. No.: 08/855,768

[22] Filed: Apr. 22, 1997

[51] Int. Cl.[6] ..... A01H 5/00

[52] U.S. Cl. ..... Plt./259

[58] Field of Search ..... Plt./100, 259

*Primary Examiner*—Howard J. Locker

*Attorney, Agent, or Firm*—Ladas & Parry

[57] ABSTRACT

A new and distinct hybrid plant named 'Himalaya' (*Mentha arvensis*) characterized by its higher yield of oil which is rich in menthol, improved regeneration potential, vigorous growth, deep green broad thick leaves, pinkish white flowers and tolerance to rust such as alternaria leaf blight, corynespora leaf spot and powdery mildew.

1 Drawing Sheet

FIELD OF THE INVENTION

The present invention relates to a new plant variety namely *Mentha arvensis* 'Himalaya'.

BACKGROUND OF THE INVENTION

The present invention relates to a new and distinct variety of *Mentha arvensis*, a member of the mint (Mentha) genus, which is a hybrid between CIMAP/MAH-9 (cv. Gomti) and CIMAP/HY-77 (cv. Kalka). The commercial cultivation of *Mentha arvensis* is wide-spread in tropical and subtropical climates and its oil is produced and traded in larger quantities than any of the other mint oils. The crude *Mentha arvensis* oil is rarely employed in flavoring and is used as a source of natural menthol and dementholized oil. Menthol's refreshing aroma and cooling action along with its stimulant and antiseptic qualities have led to its wide-spread use for medicinal purposes in pharmaceutical industries and cosmetics. The oil and its derivatives also find extensive use in flavoring confectionery and cigarettes. In spite of the limitations of *Mentha arvensis* genotypes being sub-fertile in nature, there are no cross-incompatible barriers and, therefore, the practical feasibility exists for combining potentials of oil yield and its quality, and disease resistance by crossing prospective parental genotypes involving sexual hybridization in the breeding program. The genotype CIMAP/MAS-92-1 (Himalaya) evolved in this invention represents such an improvement combining higher oil yield and tolerance to the common diseases. This offers the growers an improved high yielding, disease tolerant variety which can be commercially cultivated to obtain higher yield of menthol rich oil.

SUMMARY OF THE INVENTION

The present invention provides a new and distinct hybrid plant named 'Himalaya' of *Mentha arvensis* characterized by its higher yield of oil which is rich in menthol; improved regeneration potential; tolerance to rust, alternaria leaf blight, corynespora leaf spot, and powdery mildew; vigorous growth; deep green broad thick leaves; and pinkish white flowers.

DETAILED DESCRIPTION OF THE INVENTION

Figure 1:
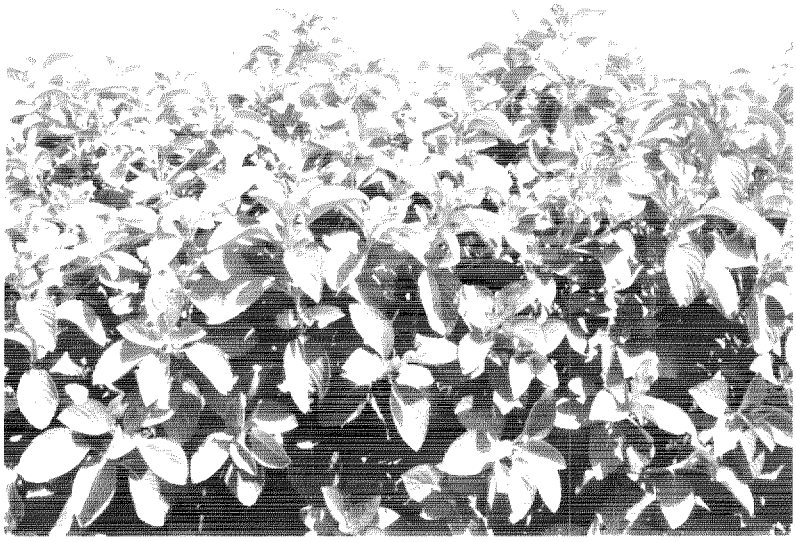

A new and distinct hybrid plant named 'Himalaya' of *Mentha arvensis* having the following combination of characters:

(a) deep green foliage with broad, thick and leathery leaves, and pinkish white flowers;
(b) regeneration potential in second harvest;
(c) resistance to leaf rust and alternaria leaf spot and toleration to corynespora leaf spot and powdery mildew;
(d) RAPD profile for PCR amplified DNA segment using twelve primers distinct from other existing varieties known to applicants, and
(e) high oil yield under different environments.

The new variety of this invention is a Japanese mint genotype, named 'Himalaya' which was created in a planned breeding program conducted by us at Central Institute of Medicinal and Aromatic Plants (CIMAP), Lucknow, India with an aim to develop a hybrid clone of *Mentha arvensis* combining the property of regenerability after first harvest of the herbage of the genotype CIMAP/MAH-9 (cv. Gomti) and tolerance to leaf spot and rust diseases of the genotype CIMAP/HY-77 (cv. Kalka). For this purpose the two genotypes were grown in alternate rows in a field plot in July 1991 at Lucknow, India facilitating pollination of CIMAP/MAH-9 flowers with CIMAP/HY-77 pollen. The seeds borne on CIMAP/MAH-9 were collected in October 1991 and were sown in pots under glasshouse conditions in December 1991. The resultant seedlings were space planted in the field at Lucknow in January 1992. Based on the superior performance for vigorous growth habit, oil yield and freedom from diseases, the plant of this invention (clone CIMAP/MAS-92-1) was selected for further observation and evaluation.

Considering the superior characteristics like excellent vigor, enhanced yield, regeneration potential and freedom from common diseases, it was asexually reproduced through stolons (suckers) to maintain clonal purity. The selected clone CIMAP/MAS-92-1 was grown in 3 meter rows along with its parents (cvs. Gomti and Kalka) for two consecutive years following uniform cultural practices to study oil yield and disease tolerance. The clone CIMAP/MAS-92-1 maintained its virogous growth, enhanced oil yield and tolerance to rust, alternaria leaf blight, corynespora leaf spot and powdery mildew.

This clone (CIMAP/MAS-92-1) was vegetatively propagated and grown in a replicated field trial (plot size 9 $m^2$, 3 replications) along with other promising genotypes and cvs. Gomti, Kalka at Lucknow, India during 1995 to study oil yield and quality over two harvests of the herbage. The genotype proved significantly superior over both parental cultivars in terms of oil yield (231 kg/ha oil). The quality of essential oil in terms of menthol content (79%) falls between the range of that of parents.

In the subsequent year (1996), the genotype (CIMAP/MAS-92-1 $)_2$ was evaluated in a replicated field trial (plot size 25 $m^2$, 3 replications) along with parents and another commercial cultivar (Shivalik) over two harvests of the herbage at two locations (Lucknow and Pantnagar) to study oil yield, quality and natural disease incidence. The clone (CIMAP/MAS-92-1) proved significantly superior over its parents and local check in both the harvests by yielding 444 kg/ha oil at Lucknow and 284 kg/ha oil at Pantnagar. The quality of the essential oil as reflected in terms of menthol content was significantly superior to the parent cv. Gomti at both locations. Like the cv. Kalka, the genotype CIMAP/MAS-92-1 was found to be free from the common diseases as compared to cv. Gomti and cv. Shivalik both at Lucknow and Pantnagar, India.

Evidence of uniformity and stability

The genotype CIMAP/MAS-92-1 has remained stable and uniform for its morphological characters and showed consistency in performance for various oil yield and quality attributes during its evaluation and vegetative multiplication since 1992.

Type and frequency of variants during reproduction and multiplication and identification of the variant:

A single variant differing only in colour of the foliage (yellowish green) from normal population of CIMAP/MAS-92-1 with deep green foliage was identified in sucker production block through vegetative multiplication in a population of 800 plants covering an area of 130 square meter in 1993. The frequency of the occurrence of the variant was 0.12%. No variant has been recovered in much larger multiplication, testing and experimental plots screened carefully in 1994, 1995, 1996 cropping seasons.

Figure 2:
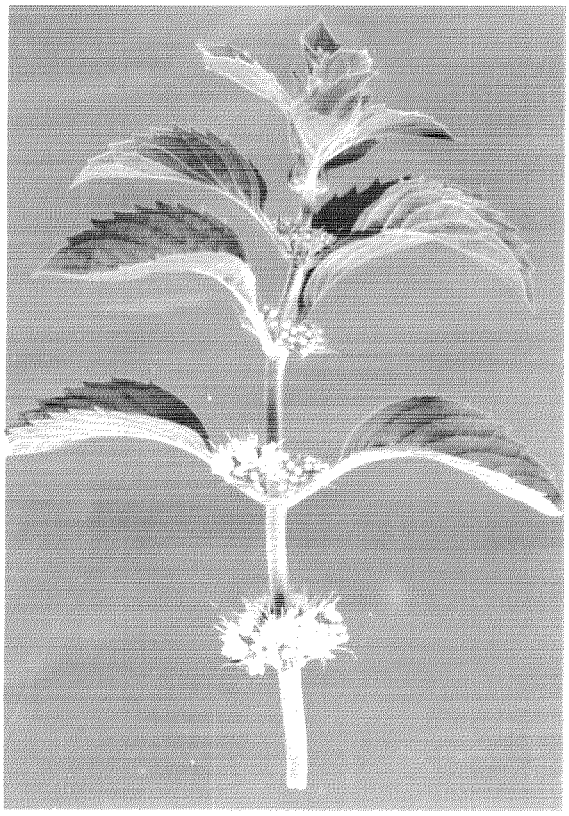

Brief description of the accompanying drawings, and in these drawings:

FIG. 1 is a photograph of field grown plants of CIMAP/MAS-92-1 (cv. Himalaya) depicting broad, deep green foilage; and FIG. 2 is a close-up colour photograph of a single flower bearing twig depicting typical pinkish white flowers on the genotype CIMAP/MAS-92-1 (cv. Himalaya).

Statement of distinction

The genotype CIMAP/MAS-92-1 processes broad, thick, leathery, deep green leaves (R.H.S. 138B) and pinkish white flowers which are quite clear from FIGS. 1 and 2 of the accompanying drawings.

The genotype CIMAP/MAS-92-1 is distinct in regeneration potential in second harvest which is reflected in significantly higher oil yield as compared to other varieties.

'Himalaya's' RAPD profile was different from those of the Kalka and Gomti cultivars and had certain features common to both.

RAPD Analysis

Using 12 random primers (MAP01 to MAP12) with following sequence description a comparison was made for five genotypes (cultivars) including CIMAP/MAS-92-1 to establish the relatedness among them.

| Primer | Base sequence | | | | | |
|---|---|---|---|---|---|---|
| MAP01 | 5' | AAA | TCG | GAG | C | 3' |
| MAP02 | 5' | GTC | CTA | CTC | G | 3' |
| MAP03 | 5' | GTC | CTT | AGC | G | 3' |
| MAP04 | 5' | TGC | GCG | ATC | G | 3' |
| MAP05 | 5' | AAC | GTA | CGC | G | 3' |
| MAP06 | 5' | GCA | CGC | CGG | A | 3' |
| MAP07 | 5' | CAC | CCT | GCG | C | 3' |
| MAP08 | 5' | CTA | TCG | CCG | C | 3' |
| MAP09 | 5' | CGG | GAT | CCG | C | 3' |
| MAP010 | 5' | GCG | AAT | TCC | G | 3' |
| MAP011 | 5' | CCC | TGC | AGG | C | 3' |
| MAP012 | 5' | CCA | AGC | TTG | C | 3' |

This analysis could facilitate narrowing down to four primers MAP03, 04, 05, 12 which, in turn, were used in genotypic pair analysis for assessing the genetic/molecular distances. Genotypes of Gomti and Kalka were observed to be closer to Himalaya. The following table gives the extent of similarity among these three genotypes in paired test.

Similarity percentage for commonality of amplified bands (paired analysis)

| | Genotypic pair | | |
|---|---|---|---|
| Primer | Himalaya and Gomti I | Gomti and Kalka II | Kalka and Himalaya III |
| MAP03 | 92.3 | 92.3 | 100.0 |
| MAP04 | 57.1 | 54.5 | 76.9 |
| MAP05 | 100.0 | 93.3 | 93.3 |
| MAP12 | 66.6 | 50.0 | 66.6 |

As evident from the similarity indices (in paired tests), Gomti and Kalka (column II) have a greater genetic distance (or lesser similarity) compared to Himalaya and Gomti pair (Column I) followed by Kalka and Himalaya pair (column III).

Further, the primer MAP03 showed 100% band similarity between Kalka and Himalaya compared to 92.3 shown by other two pairs. Similarly, MAP05 showed a closer relatedness (100% band similarity) between Himalay and Gomti compared to 93.3% by other pairs. MAP12 on the other hand shows much higher similarity of Himalaya to Gomti as well as Kalka (band similarity of 66.6%) compared to that between Gomti and Kalka (50% band similarity). These observations on percent similarity indicate the donation of genomic segments into Himalaya by Gomti and Kalka resulting into a closeness of Himalaya with both these genotypes and thus confirming that Gomti and Kalka are the parents of Himalaya.

Objective Description of the Variety Himalaya (CIMAP/MAS-92-1)

The following is an objective description of the new variety, with color terminology being in accordance with the R.H.S. Colour Chart, except where ordinary color terminology is used.

1. Genus: Mentha.
2. Species: *arensis* L.
3. Family: Lamiaceae.
4. Common name: Japanese mint/Corn mint/Menthol mint.
5. Plant height: About 70 cm.
6. Growth habit: Erect, uniform.
7. Stem: Quadrangular, hard, hairy (medium), green with light purplish tinge at the base, 5th internode 8 mm in diameter, average number of nodes in the shoot=19.
8. Leaf:
   *Texture.*—Thick.
   *Surface.*—Hairy.
   *Shape.*—Ovate.
   *Margin.*—Serrated with deep broad dents.
   *Tip.*—Acute.
   *Base.*—Attenuate.
   *Size.*—Broad.
   *Length.*—6.22 cm.
   *Width.*—3.6 cm.
   *Petiole length.*—1.5 cm.
   *Area.*—15.4 $cm^2$.
9. Leaf-stem ratio (w/w): 1.5.
10. Inflorescence:
   *Form.*—Raceme of axillary verticillasters.
   *First flowering.*—130 days.
11. Flower:
   *Pedicel.*—Purplish.
   *Calyx.*—Green and hairy.
   *Corolla.*—Pinkish white and hairy (intensity of colour increases towards corolla tube).
   *Anthers.*—Four, rudimentary, white which remain inside the corolla tube.
   *Stigma.*—Bifid.
   *Seed formation.*—Not observed.
12. Oil content in the fresh herb: 0.7.
13. Oil quality:
   *Menthol content* (%).—78–82.
   *Menthone content* (%).—4.3–8.6.
   *Isomenthone content* (%).—3.0–3.8.
   *Menthyl acetate content* (%).—0.3–6.7.
   *Congealing point.*—20–21°.

Additional Description of the variety 'Himalaya'

The variety 'Himalaya' has several morphological characters that are intermediate of those of the varieties Gomti and Kalka.

| Sl. No. | Character | Himalaya | Kalka | Shivalik | Gomti |
|---|---|---|---|---|---|
| 1. | Stem Color | Green with purple tinge at base 8.0 | Light majenta | Light majenta | Light majenta |
| | Thickness (mm) | 8.0 | 3.6 | 10.0 | 7.9 |
| 2. | Leaf lamina color | Deep green | Green | Dark green | Dark green |
| | length (cm) | 6.2 | 6.7 | 5.2 | 6.4 |
| | width (cm) | 3.6 | 2.4 | 2.8 | 3.1 |
| | area ($cm^2$) | 15.4 | 8.7 | 10.1 | 13.3 |
| | petiole length (cm) | 1.5 | 1.2 | 0.6 | 0.7 |
| 3. | Flower color | Pinkish white | White | White | White with pink marks on petals |
| 4. | Disease incidence Rust | Resistant | Resistant | Susceptible | Susceptible |
| | Alternaria leaf blight | Resistant | Resistant | Susceptible | Susceptible |
| | Corynespora leaf spot | Tolerant | Tolerant | Susceptible | Susceptible |
| | Powdery mildew | Tolerant | Susceptible | Tolerant | Tolerant |

The chromosome number of the claimed plant is 2n=96.

'Himalaya' efficiently forms suckers during the winter season and the quality of suckers produced under ideal conditions has been estimated in range of 180 to 200 Quintal/ha.

For a crop planted on 20th January the optimal harvesting date is 10th May and second harvesting date 20th July. The planting and harvesting dates accordingly, can be shifted by one week time. The oil yield and quality during the first and second harvests are as follows:

| | 1st Harvest | | 2nd Harvest | |
|---|---|---|---|---|
| Location of trial | Oil yield (Kg/ha$) | Menthol % | Oil yield (Kg/ha$) | Menthol % |
| Lucknow | 257.0 | 82.0 | 187.0 | 80.0 |
| Pantnagar | 196.0 | 78.9 | 88.0 | 80.0 |

In monoculture planting, 'Himalaya' has the ability to cover the total soil surface predominately. However, subsequent agricultural operations of disc harrowing and proper drying of the soil can be followed to eliminate the suckers completely.

Fertilizer requirements are 200:60:60 Kg/ha of $N_2$:$P_2O_5K_2O$ at Lucknow and 150:40:40 Kg/ha of $N_2$:$P_2O_5K_2O$ at Pantnagar in the form of Urea: Single super phosphate: Murate of potash.

Additional description of *Mentha arvensis* (CIMAP/MAS-92-1) cv Himalaya

1. Stem colour: Green (143C), Lower part purple (70A) pigmented.
2. Internode length: 4.5 cm at $5^{th}$ internode.
3. Leaf colour: Deep green (138B).
4. Average trichome number per leaf: 13,500,000.
5. Pedicel colour: purplish (70B).
6. Pedicel length: 3.72 mm.
7. Calyx colour: Green(141C).

8. Corolla: Pinkish white colour(56D) and 3.47 mm long.

9. Suckers: White. Brittle.

Comparison with other varieties of the same botanical and market class of *Mentha arvensis*

| Character | cv. MAS-1 | cv. Kalka | cv. Shivalik | cv. Gomti | cv. Himalaya |
|---|---|---|---|---|---|
| 1. Plant height (cm) | 53 | 60 | 65 | 90 | 70 |
| 2. Leaf: stem ratio | 1.2 | 1.0 | 0.8 | 1.0 | 1.5 |
| 3. Stem | | | | | |
| •color | Upper green (141C), lower pigmented red purple (71B) | GREEN (141C), lower pigmented red purple (71B) | Green (141B) lower pigmented red purple (71B) | Green (143B) lower pigmented purple (77A) | Green (143C) lower purplish (70A) |
| •Stiffness | Hard | Hard | Woody | Woody | Hard |
| •Thickness internode (mm) | 6.8 at 5th | 3.6 | 10.0 | 7.9 | 8.0 |
| 4. Leaf | | | | | |
| •Color | Green (139C) | Green (139C) | Green (138A) | Green (138A) | Green (138B) |
| •Length (cm) | 6.46 | 6.7 | 5.2 | 6.4 | 6.2 |
| •Width (cm) | 2.3 | 2.4 | 2.8 | 3.1 | 3.6 |
| •Area ($cm^2$) | 8.2 | 8.7 | 10.1 | 13.3 | 15.4 |
| 5. Petiole length (cm) | 1.1 | 1.2 | 0.6 | 0.7 | 1.5 |
| 6. Flower color | Whitish | Whitish | Whitish | Whitish | Pinkish white (56 D) |
| 7. Flower length (mm) | 3.72 | 3.48 | 4.66 | 4.74 | 3.72 |
| 8. Calyx color | Green (143B) with red purple streaks (71B) | Green (143B) with red purple streaks (71B) | Green (141B) | Green (141B) | Green (143C) |
| 9. Stigma color | White | White | Purplish (71C) | Purplish (71C) | White |
| 10. Oil content (%) | 0.75 | 0.70 | 0.60 | 0.40 | 0.70 |
| 11. Herb yield/ plant (g) | 57.7 | 120.7 | 132.9 | 157.7 | 156.0 |
| 12. Oil yield/ plant (mg) | 204 | 369 | 363 | 207 | 495 |
| 13. Menthol (%) | 84 | 82 | 76 | 74 | 80 |
| 14. Avg. trichomes per leaf (×1000) | 785 | 1178 | 804 | 1024 | 1350 |
| 15. Trichome ratio (lower/ upper) | 1.92 | 2.85 | 2.15 | 2.49 | 3.36 |
| 16. Disease incidence to | | | | | |
| •Rust | Tolerant | Resistant | Susceptible | Susceptible | Resistant |
| •Alternaria leaf blight | — | Resistant | Susceptible | Susceptible | Resistant |
| •Corynespora leaf spot | Susceptible | Tolerant | Susceptible | Susceptible | Tolerant |
| •Powdery mildew | Susceptible | Susceptible | Tolerant | Tolerant | Tolerant |

The color specifications of the plant parts distinguishing Himalaya from others within the same botanical and market class have been incorporated according to R.H.S. Colour Chart published by The Royal Horticultural Society, 80 Vincent Square, London SW1P 2PE.1995. The distinguishing characteristics are compared with other cultivars of same botanical and market class emphasize the distinctiveness of 'Himalaya'.

The genotype CIMAP/MAS-92-1 ('Himalaya') was bred at the Central Institute of Medicinal and Aromatic Plants (CIMAP) under the genetic improvement program on mints. The complete RAPD profile for PCR amplified DNA segments using 12 primers (MAP01 to MAP12) is available providing evidence of distinctiveness of the genotype of Himalaya.

SEQUENCE LISTING

```
<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 1
```

-continued aaatcggagc 10

<210> SEQ ID NO 2
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 2 gtcctactcg 10

<210> SEQ ID NO 3
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 3 gtccttagcg 10

<210> SEQ ID NO 4
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 4 tgcgcgatcg 10

<210> SEQ ID NO 5
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 5 aacgtacgcg 10

<210> SEQ ID NO 6
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 6 gcacgccgga 10

<210> SEQ ID NO 7
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 7 caccctgcgc 10

-continued

<210> SEQ ID NO 8
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 8 ctatcgccgc 10

<210> SEQ ID NO 9
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 9 cgggatccgc 10

<210> SEQ ID NO 10
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 10 gcgaattccg 10

<210> SEQ ID NO 11
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 11 ccctgcaggc 10

<210> SEQ ID NO 12
<211> LENGTH: 10
<212> TYPE: DNA
<213> ORGANISM: Artificial Sequence
<220> FEATURE:
<221> NAME/KEY: primer _bind
<223> OTHER INFORMATION: random primer for comparing plant genotypes

<400> SEQUENCE: 12 ccaagcttgc 10

We claim:

1. A new and distinct variety of hybrid *Mentha arvensis* plant, as described and illustrated, and having the following characteristics:

(a) the hybrid being a cross between two *Mentha arvensis* cultivars, CIMAP/MAH-9 (cv. Gomti) and CIMAP/HY-77 (cv. Kalka),
(b) the hybrid having deep green (138B), broad, leathery leaves,
(c) the hybrid having an inherited regeneration quality in second harvest from the female parent CIMAP/MAH-9 (cv. Gomti),
(d) the hybrid being resistant to leaf rust and alternaria leaf blight and tolerant to corynospora leaf spot and powery mildew and
(e) the hybrid having a unique RAPD profile against the primers MAP01 to MAP12.

* * * * *

UNITED STATES PATENT AND TRADEMARK OFFICE

CERTIFICATE OF CORRECTION

PATENT NO. : PP 10,935
DATED : June 1, 1999
INVENTOR(S) : Sushil Kumar et al.

It is certified that error appears in the above-identified patent and that said Letters Patent is hereby corrected as shown below:

Title page,
Item [54], "MINI" should read -- MINT --.
Insert -- [30] Foreign Application Priority Data
Feb. 28, 1997 [IN] India 516/DEL/1997 --.

Signed and Sealed this

Twenty-fourth Day of September, 2002

*Attest:*

*Attesting Officer*

JAMES E. ROGAN
*Director of the United States Patent and Trademark Office*